United States Patent [19]

Post et al.

[11] Patent Number: 4,794,204
[45] Date of Patent: Dec. 27, 1988

[54] PROCESS FOR THE REMOVAL OF DIMETHYL ETHER IN METHYL CHLORIDE

[75] Inventors: Hendrik W. Post, Hofheim am Taunus; Helmold von Plessen, Königstein/Taunus; Wilhelm Lendle, Bad Soden am Taunus, all of Fed. Rep. of Germany

[73] Assignee: Hoechst Aktiengesellschaft, Fed. Rep. of Germany

[21] Appl. No.: 61,793

[22] Filed: Jun. 11, 1987

[30] Foreign Application Priority Data

Jun. 14, 1986 [DE] Fed. Rep. of Germany ....... 3620069

[51] Int. Cl.$^4$ .................... C07C 17/38; C07C 19/02
[52] U.S. Cl. ................................. 570/262; 570/258; 570/259
[58] Field of Search ................ 570/262, 259, 258

[56] References Cited

U.S. PATENT DOCUMENTS

| 1,920,846 | 8/1933 | Daudt | 570/259 |
| 2,153,170 | 4/1939 | Buc et al. | 570/262 |
| 3,484,494 | 12/1969 | Carson | 570/258 |
| 4,220,609 | 9/1980 | McEntee et al. | 570/262 |
| 4,307,260 | 12/1981 | Moore et al. | 570/262 |

FOREIGN PATENT DOCUMENTS

| 213782 | 5/1968 | U.S.S.R. | 570/262 |
| 873873 | 8/1961 | United Kingdom | 570/262 |

Primary Examiner—J. E. Evans
Attorney, Agent, or Firm—Connolly and Hutz

[57] ABSTRACT

A process is described for the removal of dimethyl ether in methyl chloride by catalytic cleavage by means of hydrogen chloride. Dimethyl ether is present as an impurity in crude methyl chloride produced by the catalytic esterification of methanol. The crude methyl chloride is cooled so that water and hydrogen chloride separate out. Gaseous hydrogen chloride is then added to the methyl chloride in an amount corresponding to at least twice the molar amount of dimethyl ether, and the gaseous mixture is passed over a methanol esterification contact catalyst at an elevated temperature.

2 Claims, 1 Drawing Sheet

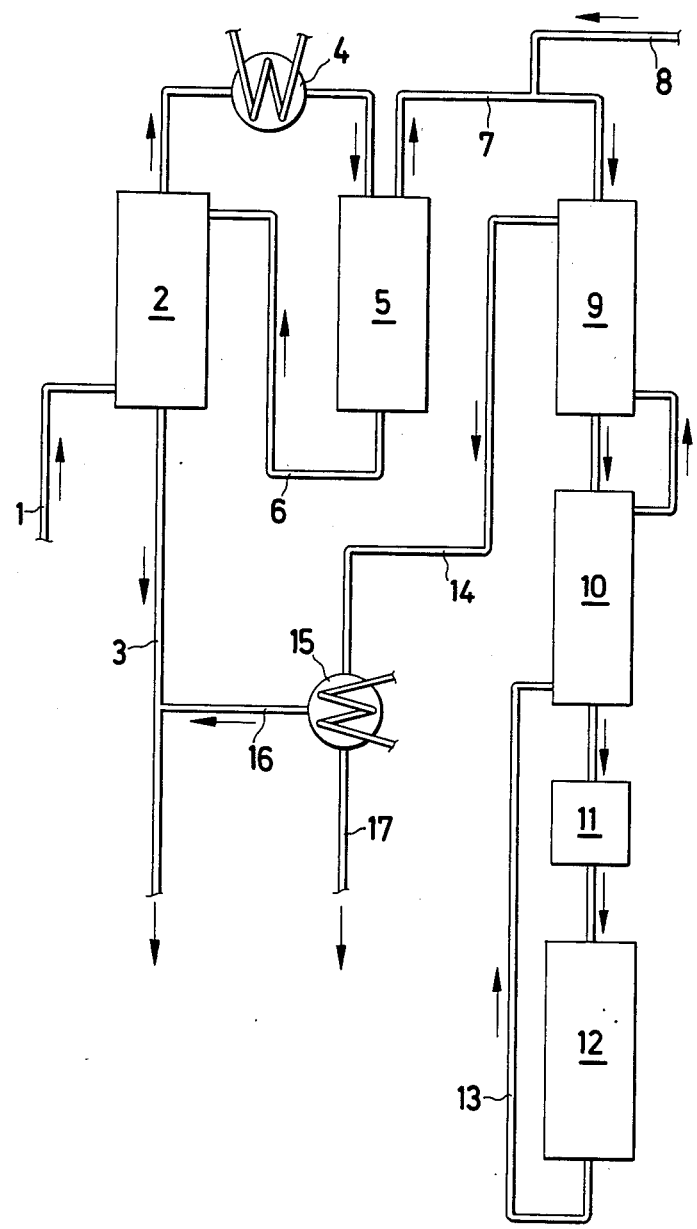

PROCESS FOR THE REMOVAL OF DIMETHYL ETHER IN METHYL CHLORIDE

The present invention relates to a process for the removal, by catalytic cleavage by means of hydrogen chloride, of dimethyl ether from crude methyl chloride produced by the catalytic esterification of methanol.

An important process for the preparation of methyl chloride is based on the esterification of methanol with hydrogen chloride at an elevated temperature over a solid catalyst. In general, the reaction is carried out at 350° to 400° C., and an aluminum oxide catalyst is used. The reaction which takes place in this process is described by the following equation.

$$CH_3OH + HCl \rightarrow CH_3Cl + H_2O$$

Varying amounts of dimethyl ether (DME) are formed as a by-product and are removed from the reaction zone together with the gaseous methyl chloride. After the gas mixture has been cooled to room temperature and the water has been condensed, the residual methyl chloride still contains methanol (less than 0.03%), 0.3 to 2% of DME, less than 2% of hydrogen chloride and approx. 0.1% of water. Usually, this crude methyl chloride is washed, and thereby dried, with sulfuric acid containing at least 80% by weight of $H_2SO_4$. In the course of this, the sulfuric acid fixes not only the residual water, but also traces of methanol and almost the whole of the dimethyl ether. In most cases 95% strength sulfuric acid is used for the drying process. When it has become exhausted, the wash acid, which then is still approx. 80% strength and contains 5 to 10% of (bound) DME, has to be worked up.

Working up this waste sulfuric acid is an environmental problem difficult to solve, and several processes have been suggested for its solution. Thus, in accordance with German Offenlegungsschrift No. 3,151,691 for example, it is possible to subject the waste sulfuric acid to steam distillation at the boil and to pass the condensed vapors to a biological effluent purification plant in order to remove their organic constituents. The recovered sulfuric acid can be concentrated and, if necessary, further purified.

Since DME is a contamination it has to be removed from the crude methyl chloride. In view of the similar boiling points a removal by distillation is difficult. It was therefore necessary to find an improved process for the removal of DME from crude methyl chloride.

A process has now been found for the removal of dimethyl ether from methyl chloride by catalytic cleavage by means of hydrogen chloride, wherein the dimethyl ether is present as an impurity in crude methyl chloride produced by the catalytic esterification of methanol, the crude methyl chloride is cooled, so that hydrogen chloride at least in part and water separate out, the methyl chloride in admixture with gaseous hydrogen chloride is passed over a methanol esterification contact catalyst at an elevated temperature, the molar ratio of hydrogen chloride/DME being at least 2:1. The higher this ratio the lower the attainable residual content is of DME. Molar ratios of from 2:1 to 10:1 are preferred.

The process according to the invention makes it possible to reduce substantially the amount of dimethyl ether remaining in the methyl chloride. If further purification with sulfuric acid is carried out, there is a marked reduction in the amount of sulfuric acid required and of condensate produced containing organic impurities which must be disposed of.

A description of the esterification of methanol is to be found in Winnacker-Küchler, Chemische Technologie ("Chemical Technology"), volume 6 (1982), page 4.

It is known from U.S. Pat. No. 2,084,710 to cleave dialkyl ethers with aqueous hydrochloric acid and zinc chloride, with the formation of alkyl chlorides. However, this process is carried out in the liquid aqueous phase in the absence of excess alkyl chloride and at relatively low temperatures. In contrast with this, the cleavage of the mixture containing dimethyl ether is carried out by the process according to the invention at fairly high temperatures, in particular 130° to 450° C., preferably 150° to 400° C., in the presence of large amounts of methyl chloride. It is preferred if the lower limit of the temperature range used is at 200° C., especially 250° C. A preferred upper limit is below 350° C., especially below 300° C. With decreasing temperature decreases the formation of soot, low temperatures make necessary a more active catalyst or longer residence times.

The methanol esterification contact catalysts employed in this process are also capable of cleaving dimethyl ether in the presence of hydrogen chloride. It is possible to use, for example, iron(III) chloride, zinc chloride, cadmium chloride, aluminum oxide and zeolites. Contact catalysts free from heavy metals are preferred, especially aluminum oxide. It is surprising that the low DME content of the crude methyl chloride can be reduced considerably in the process according to the invention by repeated treatment with the catalyst and that even DME-contents in the ppm-range can be obtained.

After the dimethyl ether has been cleaved in accordance with the invention, the treated gas can be cooled again in order to deposit water and hydrogen chloride. The gas freed from dimethyl ether can then be washed with sulfuric acid of a concentration of approx. 80 to 96% by weight of $H_2SO_4$, and the last traces of DME and water can be removed. In this case too, the content of (bound) DME in the wash acid should not exceed 5 to 10%.

The performance of the process is illustrated in greater detail by means of the FIGURE.

The gas mixture coming from the methanol esterification reaction at approx. 300° C. is fed through line (1) into the packed column (2) and is there scrubbed with 35–40% strength hydrochloric acid. In the course of this, the gas is cooled to 125° C. A 20–25% strength hydrochloric acid (quench acid) is formed at the same time and is removed through line (3). The gas mixture is then cooled further to 40°–45° C. in a graphite cooler (4). Condensed water and hydrogen chloride are separated off as 35–40% strength hydrochloric acid and accumulate in the container (5). This hydrochloric acid is recycled to the packed column (2) through line (6). The crude gas leaves the container (5) through line (7). In addition to dimethyl ether, it still contains 0.1 to 0.2% of water and 0.3 to 4% of hydrogen chloride. Hydrogen chloride can be added through line (8) in order to increase the molar ratio of hydrogen chloride to dimethyl ether. At an average dimethyl ether content of 0.5% by volume, the HCl content is adjusted to at least 1% by volume. The gas passes into a graphite heat exchanger (9), then into a further heat exchanger (10) made of nickel and finally into a heating unit (11), composed of nickel, in which it is heated up to a reaction temperature between 150° and 400° C. It is then passed over the catalyst in the reactor (12). The reaction mixture formed is passed through line (13) into the heat exchanger (10) and then into the heat exchanger (9). There it transfers its heat content to the inflowing gas. The reaction mixture leaves (9) through line (14). After final cooling with water in a graphite heat exchanger (15), water and hydrogen chloride are again separated off as hydrochloric acid through line (16). The hydrochloric acid flows through line (16) to line (3). The treated gas is passed through line (17) to sulfuric acid washing (not shown).

It is also possible to perform the esterification of methanol with increased portions of HCl so that after condensation of water still free HCl (e.g. from 1 to 6% vol.) are present. In this case a further addition of HCl is not necessary.

When performing the process on a large scale for longer periods of time at temperatures of at least 400° C. partial decomposition under formation of soot is observed. In this case it is useful to use $Al_2O_3$ catalysts (Harshaw) at 130° to 300° C., expecially 200° to 250° C.

The invention is illustrated further by means of the following example.

EXAMPLE

An apparatus composed of a preheater, an electrically heated reactor, several condensers and a gas washing apparatus was constructed. The amount of gas issuing was measured by a gasometer.

The preheater used was a glass flask located in a heating bath. The adjoining electrically heated reactor was composed of a nickel tube packed with catalyst (length 700 mm, diameter 50 mm). Aluminum oxide made by Alcoa (catalyst F-1/¼-6) was used as the catalyst which is recommended for esterification of methanol with HCl.

The experimental temperatures were 340° to 360° C. Downstream there was an air condenser made of glass and then a condenser operated by a liquid at 0° C. and also made of glass. A small packed column fed with water (200 ml/hour) was used as a gas washer to remove hydrogen chloride. The composition of the gases entering and leaving was determined by gas chromatography. The amounts of methyl chloride, hydrogen chloride and dimethyl ether are to be found in the following table.

| Inputs | $CH_3Cl$ mol/hr. | HCl present in the crude $CH_3Cl$, mol/hr. | HCl added, mol/hr. | DME mol/hr. |
|---|---|---|---|---|
| Test 1 | 5.30 | 0.022 | — | 0.061 |
| Test 2 | 5.35 | 0.083 | 0.087 | 0.036 |
| Test 3 | 5.39 | 0.086 | 0.462 | 0.037 |
| Test 4 | 5.36 | 0.122 | 1.203 | 0.030 |

| Yields | $CH_3Cl$ mol/hr. | HCl mol/hr. | DME mol/hr. | Temperature of test | Duration of test |
|---|---|---|---|---|---|
| Test 1 | 5.35 | approx. 0.0 | 0.0073 | 352° C. | 1 h |
| Test 2 | 5.38 | approx. 0.1 | 0.0033 | 342° C. | 2 h |
| Test 3 | 5.42 | approx. 0.5 | 0.0011 | 359° C. | 1 h |
| Test 4 | 5.39 | approx. 1.3 | 0.0003 | 358° C. | 3 h |

| | $\dfrac{\text{mol of HCl}}{\text{mol of } CH_3Cl}$ in the feed mixture | $\dfrac{\text{mol of DME (end product)}}{\text{mol of DME (feed mixture)}}$ |
|---|---|---|
| Test 1 | 0.004 | 0.12 |
| Test 2 | 0.032 | 0.09 |
| Test 3 | 0.102 | 0.03 |
| Test 4 | 0.247 | 0.01 |

It is found that the dimethyl ether content present in the crude methyl chloride can be reduced by 88 to 99% by means of the process according to the invention.

We claim:

1. A process for the removal of dimethyl ether in methyl chloride by catalytic cleavage by means of hydrogen chloride, wherein 0.3 to 3.0 percent dimethyl ether is present as an impurity in crude methyl chloride produced by the catalytic esterification of methanol, the crude methyl chloride is cooled, so that hydrogen chloride at least in part and water separate out, the methyl chloride in admixture with gaseous hydrogen chloride is passed over a methanol esterification contact catalyst at an elevated temperature the molar ratio of hydrogen chloride/dimethyl ether being at least 2:1, wherein aluminum oxide is employed as the esterification catalyst, wherein the gas passed over the methanol esterification contact catalyst is cooled again in order to deposit water and hydrogen chloride and wherein the gas freed from water and hydrogen chloride is then washed with sulfuric acid having concentration of approx. 80 to 96% by weight of $H_2SO_4$, in order to remove the last traces of dimethyl ether.

2. The process as claimed in claim 1, wherein the reaction is carried out at temperatures from 250° to 400° C.

* * * * *